United States Patent
Xu (10) Patent No.: US 10,368,579 B2
(45) Date of Patent: Aug. 6, 2019

(54) MICROVAPORIZER QUICK-RELEASE MECHANISM

(71) Applicant: Yongjie James Xu, Richmond, VA (US)

(72) Inventor: Yongjie James Xu, Richmond, VA (US)

( * ) Notice: Subject to any disclaimer, the term of this patent is extended or adjusted under 35 U.S.C. 154(b) by 149 days.

(21) Appl. No.: 15/583,828

(22) Filed: May 1, 2017

(65) Prior Publication Data

US 2018/0310614 A1   Nov. 1, 2018

(51) Int. Cl.
| A24F 47/00 | (2006.01) |
| H05B 3/06 | (2006.01) |
| A61M 15/06 | (2006.01) |
| B67D 7/02 | (2010.01) |

(52) U.S. Cl.
CPC .......... *A24F 47/004* (2013.01); *A24F 47/002* (2013.01); *A24F 47/006* (2013.01); *A24F 47/008* (2013.01); *A61M 15/06* (2013.01); *B67D 7/0294* (2013.01); *H05B 3/06* (2013.01); *H05B 2203/021* (2013.01)

(58) Field of Classification Search
CPC .............................. B67D 7/0294; A61M 15/06
USPC ..... 251/144, 149.7; 141/335, 336, 348, 351; 131/329
See application file for complete search history.

(56) References Cited

U.S. PATENT DOCUMENTS

| 4,692,590 A | * | 9/1987 | Spector | A24F 47/008 |
| | | | | 219/260 |
| 4,957,483 A | * | 9/1990 | Gonser | A61C 1/18 |
| | | | | 251/149.7 |
| 6,644,515 B1 | * | 11/2003 | Campbell | B01D 53/0407 |
| | | | | 137/43 |
| 7,476,368 B2 | * | 1/2009 | Sargent | A61L 2/10 |
| | | | | 134/166 R |
| 10,111,469 B2 | * | 10/2018 | Zhu | A24F 47/008 |
| 2004/0025968 A1 | * | 2/2004 | Allen | B67D 7/005 |
| | | | | 141/351 |
| 2015/0257447 A1 | * | 9/2015 | Sullivan | A24F 47/008 |
| | | | | 131/329 |
| 2015/0377402 A1 | * | 12/2015 | Boothe | F16L 55/1015 |
| | | | | 251/149.7 |
| 2016/0023227 A1 | * | 1/2016 | Scott | B05B 11/0097 |
| | | | | 141/2 |
| 2016/0073692 A1 | * | 3/2016 | Alarcon | A24F 47/008 |
| | | | | 131/329 |
| 2017/0064997 A1 | * | 3/2017 | Murison | A24F 15/12 |
| 2017/0341850 A1 | * | 11/2017 | Sebastian | A24B 15/16 |
| 2018/0029866 A1 | * | 2/2018 | Scott | A24F 47/002 |
| 2018/0084830 A1 | * | 3/2018 | Xu | A24F 47/008 |

* cited by examiner

*Primary Examiner* — Matthew W Jellett
(74) *Attorney, Agent, or Firm* — Nixon & Vanderhye P.C.

(57) ABSTRACT

Quick-release mechanism of a microvaporizer having a quick-release cartridge coupled to a quick-release atomizer assembly by engaging a root portion of the quick-release cartridge with a receiver mechanism in the quick-release atomizer assembly, moving a trapdoor in the quick-release cartridge, and locking the root portion in the receiver mechanism. The quick-release cartridge is provided with at least one groove or depression on a root portion extension that can be inserted into and locked with the receiver mechanism.

22 Claims, 4 Drawing Sheets

MICROVAPORIZER QUICK-RELEASE MECHANISM

This invention relates to a cartridge and an atomizer assembly for a microvaporizer, in particular a quick-release cartridge adapted to couple with a corresponding quick-release atomizer assembly to form a quick-release mechanism for the installation of a cartridge in a microvaporizer.

BACKGROUND OF THE INVENTION

A microvaporizer, such as a personal vaporizer, an inhaler or an electronic cigarette (also called an "e-cigarette"), includes a mouthpiece, a heating element (also called an "atomizer"), a tank, and a battery. The microvaporizer can be cylindrical, rectangular, hexagonal, and other applicable shapes. The tank stores liquids that would be vaporized by the atomizer to create vapor for a user. For an e-cigarette, the fluid is also called "e-liquids". The heating element is typically a heating coil that is put in contact with the liquid when vapors are desired, and is typically provided within an atomizer assembly that includes a support structure and optionally an air flow controller. The tank is typically attached to the atomizer on one end, and directly or indirectly attached to the body of the microvaporizer. The tank is can also be attached to the mouthpiece. Some of the commercial tanks also include the heating coil placed permanently inside a portion of the tank for vaporization of the liquid stored in the tank.

Conventionally, the tank is a permanent structure of the microvaporizer that stores the liquids. Alternatively, the tank can be replaced by disposable cartridges. The cartridges are typically connected to the atomizer portion of the microvaporizer via a screw thread to provide a tight seal and lock between the cartridge and the atomizer assembly. If the thread grooves are not matched accurately, or if the threads deteriorated for any reason, there would be a high possibility of fluid leakage from the connection.

The inventive quick-release mechanism improves a user's ease for connecting a cartridge to a atomizer assembly, and provides improvements in liquid seals that reduces the possibility of fluid leakage due to deterioration in the connection.

BRIEF SUMMARY OF THE INVENTION

The presently described quick-release mechanism simplifies the mechanism and process to engage a quick-release cartridge with a quick-release atomizer assembly for a microvaporizer, such as a personal vaporizer, an inhaler and an e-cigarette.

An embodiment of a quick-release cartridge that includes the presently described quick-release mechanism has an outer casing, an inner casing radially inside of the outer casing, a top surface and a bottom surface of the cartridge, a fluid storage chamber defined between the outer casing and the inner casing, at least one fluid opening provided in the inner casing located in close proximity to the bottom surface, a groove or depression provided on a root portion extension located in close proximity to the bottom surface, and a spring-loaded trapdoor that abuts the radially inner surface of the inner casing.

An embodiment of an example quick-release mechanism includes a quick-release cartridge having a groove or depression provided on an extended root portion at the bottom end of the cartridge; and a quick-release atomizer assembly having a base portion, a heating element with a heating element extension that extends away from the base portion, and a receiver mechanism. At a resting position, the quick-release cartridge and quick-release atomizer assembly are separated. At an engaged position, the cartridge is coupled to the atomizer assembly, and the groove or depression and the receiver mechanism are locked together for a secured connection.

A method to engage an exemplary quick-release mechanism involves providing a cartridge and an atomizer assembly for a microvaporizer, inserting a heating element extension from the atomizer assembly into a passage radially inwards of an inner casing of the cartridge, pushing a spring-loaded trapdoor in an axial direction towards the top of the cartridge when the heating element extension is inserted, exposing at least one fluid opening in the inner casing when the spring-loaded trapdoor is pushed, inserting an extended root portion of the cartridge into a receiver mechanism in the atomizer assembly, and holding the extended root portion in place in the receiver mechanism.

The quick-release mechanism is disengaged by an axial movement of a collar on the radially outer periphery of the receiver mechanism in the quick-release atomizer assembly to unlock the extended root portion from the receiver mechanism.

DETAILED DESCRIPTION OF THE INVENTION

A quick-release mechanism of the present invention includes a quick-release cartridge and a quick-release atomizer assembly. The quick-release mechanism allows the user to quickly attach and release the cartridge from the atomizer assembly. The quick-release mechanism also reduces the seal deterioration issue by using structures that simultaneously move a spring-loaded trapdoor in the cartridge to open a fluid opening, and insert a root portion of the cartridge into a receiver mechanism in the atomizer assembly.

The quick-release mechanism utilizes a collar on the atomizer assembly to hold together the cartridge and atomizer assembly when they are connected, and release the cartridge from the atomizer assembly when they are disengaged. In an embodiment, the collar is provided along the radially outward periphery of the atomizer assembly to act as a switch to lock or release a root portion of the cartridge from the receiver mechanism in the atomizer assembly. When the cartridge and atomizer assembly are being connected, a locking component, such as a ring or a ball, in the receiver mechanism is moved into the groove or depression and the collar is moved axially towards the cartridge to hold the locking component in the groove or depression. When the cartridge and atomizer assembly is being disconnected, the collar is moved axially away from the cartridge, which allows the locking component to be released from the groove or depression. The collar not only further supports the connection between the cartridge and the atomizer assembly, it may also act as an additional seal to prevent liquid leakage from the connection.

To further hold the root portion in place, the receiver mechanism has a spring provided in a spring chamber, the spring chamber is sealed by a chamber hatch that can depress the spring when the chamber hatch is pushed by an extension of the root portion inwards into the spring chamber. The insertion of the root portion extension also can act as an additional seal in the connection between the quick-release cartridge and the quick-release atomizer assembly.

Exemplary structures of the quick-release cartridge and the quick-release atomizer are shown in the figures. For the purposes of clarity, similar parts in the figures are given similar numbers. However, the figures are only showing simplified examples of the quick-release cartridge and quick-release atomizer assembly for clarity in showing and describing the working parts in the quick-release mechanism. The examples may have alternative embodiments that are not exactly as shown. For example, there can be additional seals provided in the quick-release cartridge and quick-release atomizer assembly that are not described and shown in the figures.

Figure 1A:
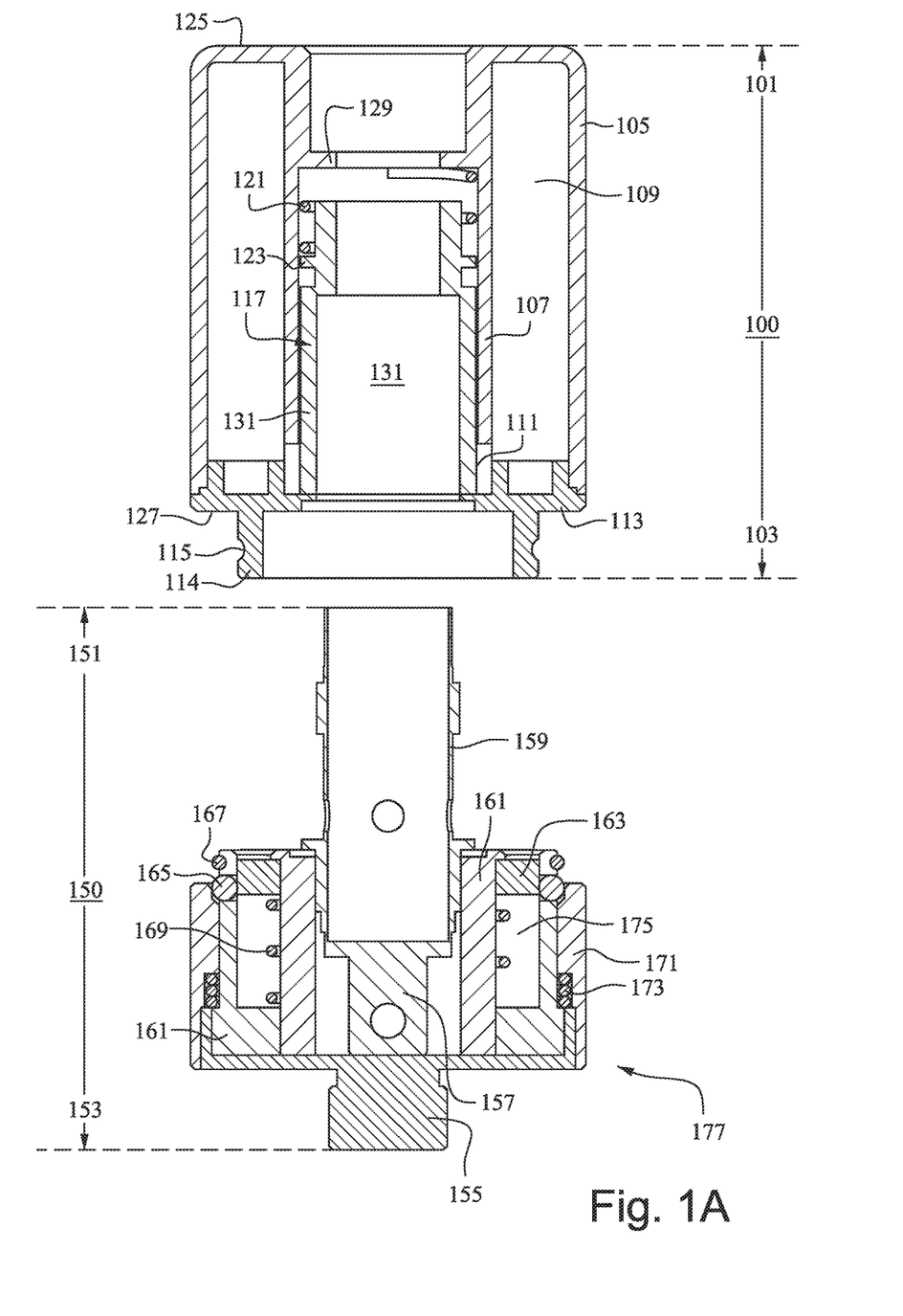
FIG. 1A is a schematic cross-sectional view of an embodiment quick-release mechanism at a resting position, in which a cartridge and an atomizer assembly are not connected.
Figure 1B:
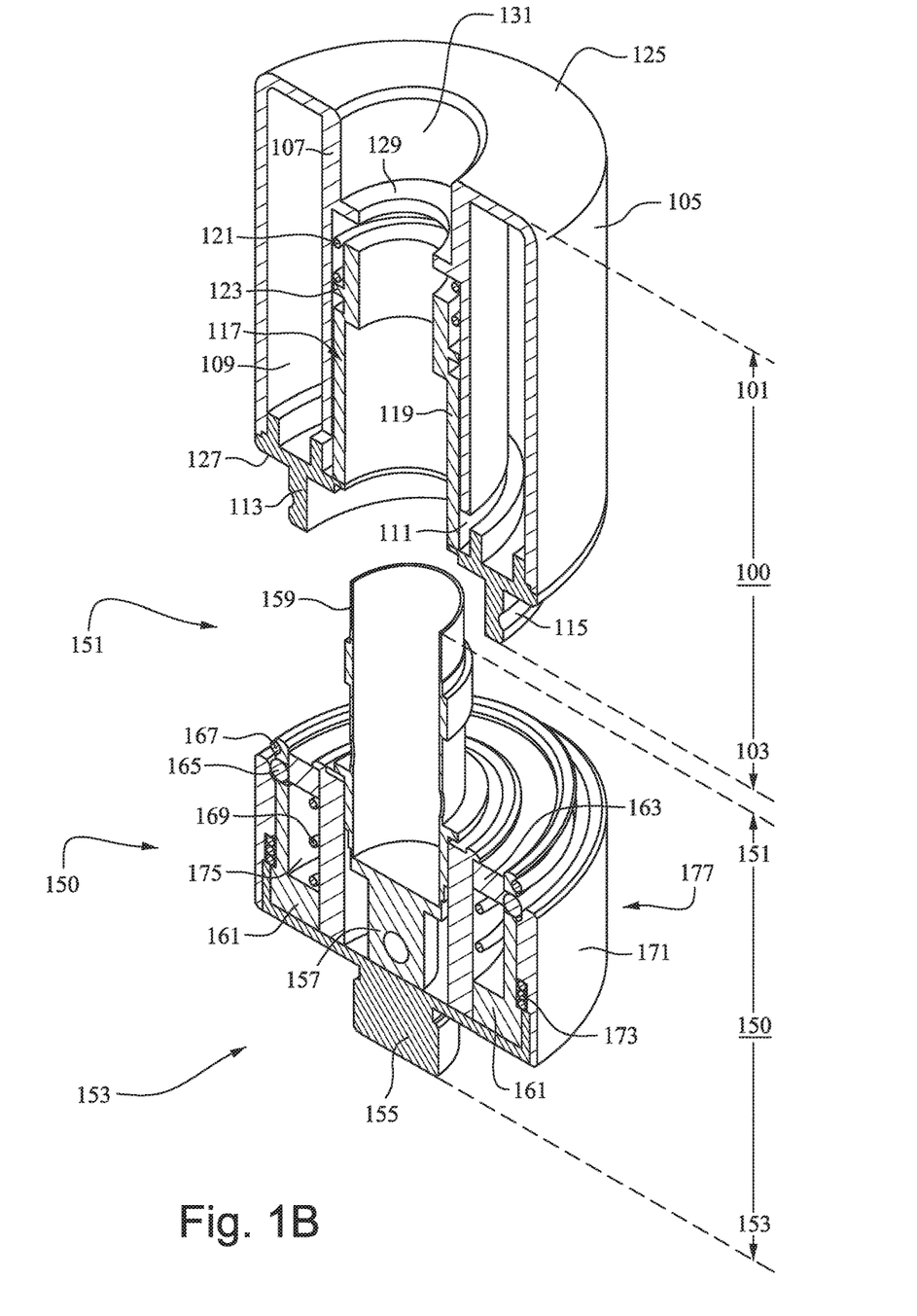
FIG. 1B is a schematic perspective cross-sectional view of the embodiment quick-release mechanism of FIG. 1A.
Figure 2A:
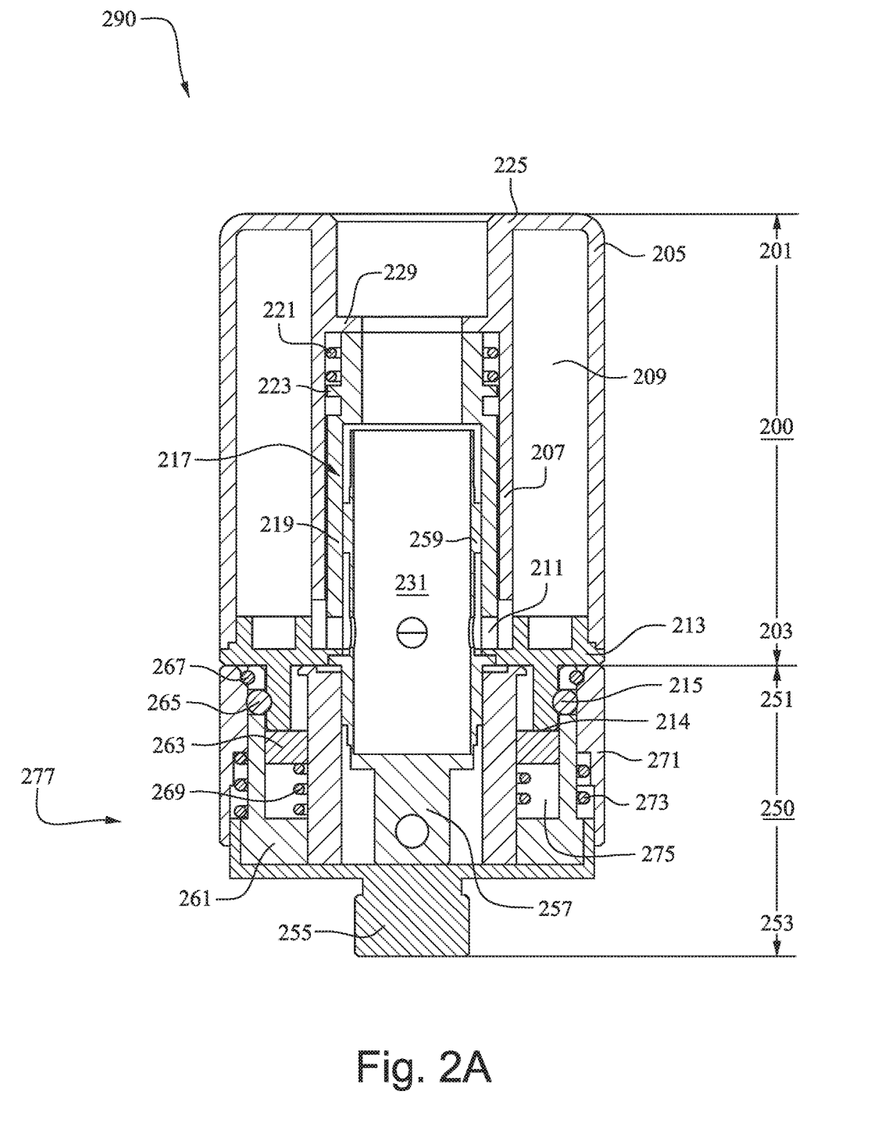
FIG. 2A is a schematic cross-sectional view of an embodiment quick-release mechanism at an engaged position, in which a cartridge and an atomizer assembly are connected.
Figure 2B:
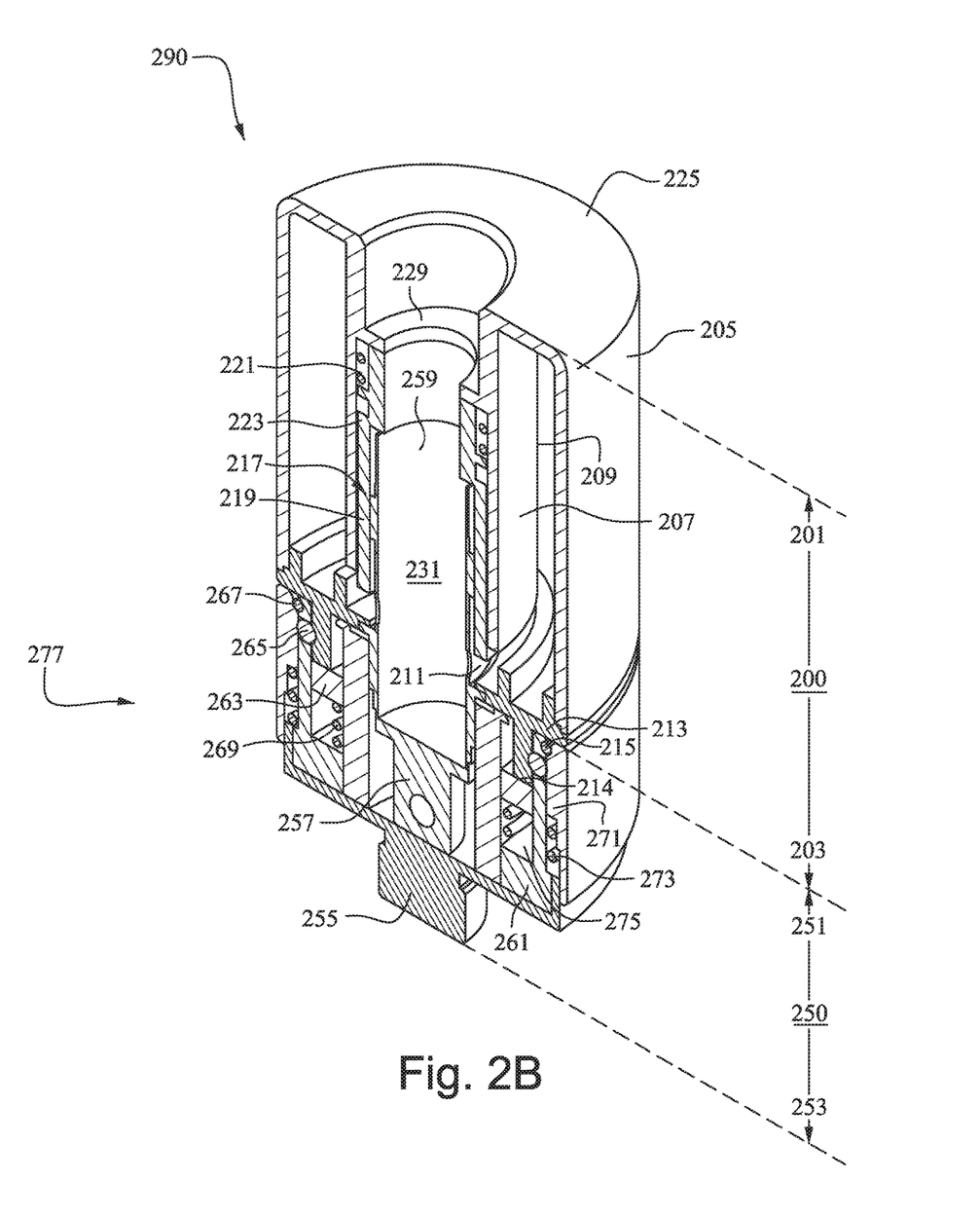
FIG. 2B is a schematic perspective cross-sectional view of the embodiment quick-release mechanism of FIG. 2A.

FIGS. 1A and 1B illustrates the inventive quick-release mechanism at a resting position (i.e., the quick-release cartridge and quick-release atomizer assembly are separated) and FIGS. 2A and 2B illustrates the inventive quick-release mechanism at an engaged position (i.e., the quick-release cartridge and quick-release atomizer assembly are interconnected).

FIGS. 1A and 1B show a cross-sectional view and a perspective cross-sectional view of an exemplary quick-release mechanism at a resting position. As shown, the exemplary quick-release cartridge is not engaged with the exemplary quick-release atomizer assembly. The quick-release cartridge 100 and the quick-release atomizer assembly 150 can be in a shape that is cylindrical, cubical, conical, or a combination thereof. The quick-release mechanism refers to the parts and method to engage the portions of the quick-release cartridge and quick-release atomizer assembly that connects the cartridge and atomizer assembly.

The quick-release cartridge 100 has a top end 101 and a bottom end 103, with a top surface 125 and a bottom surface 127, respectively. The quick-release cartridge 100 is made up of an outer casing 105, an inner casing 107, a spring-loaded trapdoor 117, and a root portion 113. A through passage 131 is provided on the radially innermost portion of the cartridge 100, along the radially inner surface of the inner casing 107. A fluid storage chamber 109 is defined in between the outer casing 105 and the inner casing 107.

The root portion extension 114 has a groove or depression 115 provided on an outer surface of the root portion 113. The spring-loaded trapdoor 117 is made up of a cover plate 119 and a spring 121 that abut the radially inner surface of the inner casing 107. The cover plate 119 covers and seals a fluid opening 111 in the inner casing 107. The cover plate 119 is held in place by the root portion 113 towards the bottom end 103, and a force exerted by the spring 121 towards the top end 101. The spring 121 is placed between a protrusion 123 on the radially outer surface of the spring-loaded trapdoor 117 and a protrusion 129 on the radially inner surface of the inner casing 107. At a resting position, the force of the spring 121 pushes the cover plate 119 towards the root portion 113, to keep the cover plate 119 over the fluid opening 111. The spring 121 is compressible to allow the cover plate 119 to be pushed towards the top end 101 and expose the fluid opening 111. The spring-loaded trapdoor 117 also defines the through passage 131 on the radially inner portion of the spring-loaded trapdoor 117. The through passage 131 extends from the top end 101 to the bottom end 103.

In the embodiment shown in FIG. 1B, the cover plate 119 is cylindrical, and the spring 121 is placed such that the coil is located in between the inner surface of the inner casing 107 and surrounds the cylindrical cover plate 119.

In another embodiment, the cover plate can be in a shape and size that is placed only in proximity to the fluid opening such that the cover plate seals over the fluid opening. In a further embodiment, the spring can be formed by multiple coils that is placed in between the cover plate and the inner casing.

The quick-release atomizer assembly 150 includes an insertion end 151 and a base end 153. The atomizer assembly 150 has a base portion 155 that acts as a support for the atomizer assembly. The base portion 155 is provided towards the base end 153. A heating element 157 sits on the base portion 155 towards the intersection end 151 with a heating element extension 159 that extends further towards the insertion end 151. The heating element 157 is provided on the radially inner portion of the atomizer assembly 150, surrounded by a receiver mechanism 177 that sits on radially outer portion of the base portion 153.

The receiver mechanism 177 has a chamber support 161 that defines the structure of a receiver chamber 175. The chamber support 161 abuts the radially outer surface of the heating element 157 and the heating element extension 159. Towards the insertion end 151, the receiver chamber 175 has a movable chamber hatch 163 that covers over the receiver chamber 175. The movable chamber hatch 165 is held in place by a force of the chamber spring 169 located inside the receiver chamber 175. The spring 169 is compressible to allow the chamber hatch 163 to move inside the receiver chamber 175 in the direction towards the base portion 155 on the base end 153.

The receiver mechanism 177 includes a collar 171 that sits on the radially outer periphery of the receiver mechanism 175. A collar spring 173, situated in between the receiver chamber 175 and the collar 171, is compressed at a resting position as shown in FIGS. 1A and 1B. There are two locking components 165, 167 situated between receiver chamber 175 and the collar 171. At the resting position, the collar 171 is held back by the first locking component 165 located in close proximity to the chamber hatch 163 towards the insertion end 151. The first locking component 165 sits in an opening in the chamber support 161. A second locking component 167 is provided close to the first locking component 165, and is placed in a separate opening in the chamber support 161 that is situated in close proximity to the chamber hatch 163 towards the insertion end 151.

When the quick-release cartridge and the quick release atomizer assembly are engaged, the insertion end of the atomizer assembly directly engages with the bottom end of the cartridge such that the connection is sealed to prevent fluid leakage from the cartridge. FIGS. 2A and 2B shows a cross-sectional view and a perspective cross-sectional view of an exemplary engaged quick-release mechanism 290.

A bottom end 203 of the quick-release cartridge 200 and an insertion end 251 of the quick-release atomizer assembly 250 are coupled together in FIGS. 2A and 2B to form an engaged quick-release mechanism 250. The quick-release cartridge 200 and quick-release atomizer assembly 250 are connected to each other such that the bottom end 203 of the quick-release cartridge 200 and the insertion end 251 of the quick-release atomizer assembly 250 abut one another. In an alternative embodiment, additional sections and/or seals can be placed in between the quick-release cartridge 200 and quick-release atomizer assembly 250, for example, an additional seal layer may be attached to the bottom end 203 of the quick-release cartridge 200.

Similar to FIGS. 1A and 1B, the quick-release cartridge 200 has a fluid storage chamber 209 that is defined by an outer casing 205, an inner casing 207, a top surface 225 of the quick-release cartridge 200 at the top end 201 of the cartridge 200, and a root portion 213 at the bottom end 203 of the cartridge 200. In an embodiment, the outer casing 205, inner casing 207 and top surface 225 are formed separately as separate components which are later joined to form the fluid storage chamber 209. In another embodiment, the outer casing 205, the inner casing 207 and top surface 225 are formed as one single structure such as by using casting techniques and molding processes.

A through passage 231 is provided inwards of the inner casing 207 as a vapor path. Extending along at least a part of the through passage 231, a cover plate 219 of a spring-loaded trapdoor 217 is configured to abut the inner wall of the inner casing 207, and seals a fluid opening 211 in the inner casing 207. The cover plate 219 is held in place by a spring 221 that sits between a protrusion 223 on the inner casing 207 in the through passage 231, and the cover plate 219. The cover plate 219 is movable along the length of the through passage 231 such that the fluid opening 211 is sealed when the cover plate 219 sits along the bottom end 203 and is opened when the cover plate 219 is moved towards the top end 201. In alternative embodiments, there can be more than one protrusion that holds more than one spring in place against the cover plate.

The root portion 213 has an extension 214 that provides a groove or depression 215, which allows the quick-release cartridge 200 to connect to the quick-release atomizer assembly 250.

The quick-release atomizer assembly 250 has a base portion 255, and a receiver mechanism 277, a heating element 257, and a heating element extension 259 that are supported by the base portion 255. The receiver mechanism 277 includes a receiver chamber 275 formed by a chamber support 261, a chamber hatch 263, and a chamber spring 269. A collar 271 is provide on the outer periphery of the receiver chamber 277, supported by a collar spring 273, a first ring 265 and a second spring 267. In an alternative embodiment, the first and second rings in the receiver mechanism can be a ball mechanisms that catches onto the groove or depression. Additionally, there can be more than one groove or depression provided on the root portion extension of the quick-release cartridge that correspond to more than one ring or ball mechanism in the quick-release atomizer assembly.

The quick-release cartridge 200 and the quick-release atomizer assembly 250 are coupled together by engaging the root portion 213 on the quick-release cartridge 200 with the receiver mechanism 277 on the quick-release atomizer assembly 250. The engagement process involves at least three simultaneous movements in the quick-release cartridge 200 and the quick-release atomizer assembly 250.

To engage the quick-release cartridge 200 and the quick-release atomizer assembly 250, the process involves:

1. Inserting the root portion extension 214 into the receiver chamber 275.

The root portion extension 214 is pushed against the chamber hatch 263, which depresses the chamber spring 269 such that the chamber hatch 263 moves inwards into the receiver chamber 275. That is, the chamber hatch 263 moves from the direction of the insertion end 251 towards the direction of the base end 253 of the quick-release atomizer assembly 250.

2. Latching the root portion extension 214 to the receiver chamber 275.

When the root portion extension 214 is inserted into the receiver chamber 275, the groove or depression 215 latches onto a first ring 265 provided in the chamber support 261 in close proximity to the chamber hatch 263. The first ring 265 is controlled by the chamber hatch 263 on the radially inner side of the receiver mechanism 277, and by the collar 271 provided on the radially outer side of the receiver mechanism 277, which is on the outer periphery of the receiver chamber 275.

When the chamber hatch 263 moves towards the base end 253, i.e., inwards of the receiver chamber 275, the first ring 256 is moved radially inwardly and fall into the groove or depression 215 on the root portion extension 214. At the same time, the collar 271, which is held in the resting position towards the base end 253 by the first ring 265 that kept the collar spring 273 depressed, is released towards the insertion end 251 because the first ring 265 is no longer holding the collar 271 in place, and the collar spring 273 is decompressed. The collar 271 is then caught and held in place by a second ring 267 that is in close proximity of the first ring 265, towards the insertion end 251. The collar holds the first ring 267 in place on the groove or depression 215 when it is moved towards the insertion end 257 and held in place by the second ring 267.

3. Moving the spring loaded trapdoor 217 to expose the fluid opening 211 on the inner casing 207.

When the root portion extension 214 is inserted into the receiver chamber 275, the heating element extension 259 is also inserted into the through passage 231 inside the inner casing 207 of the quick-release cartridge 200. The heating element extension 259 is configured such that it abuts the cover plate 219 and catches on the cover plate 219. Protrusions can be provided on the surface of the cover plate 219 such that, when the heating element extension 259 is pushed into the through passage 231 towards the top end 201, the heating element extension 259 catches on the protrusions on the cover plate 219 and moves the cover plate 219 towards the top end 201. The top end 201 of the cover plate 219 is provided a spring 221 that abuts a protrusion 129 on the inner casing 207 to hold the cover plate 219 in place. The movement of the cover plate 219 depresses the spring 221 towards the protrusion 129, and exposes the fluid opening 211 on the inner casing 207 to allow fluid communication between the fluid storage chamber 209 and the heating element 157 inside the heating element extension 159. The stored fluid is provided to the heating element 157 to produce vapor.

The three steps in the engagement process can be done simultaneously by pushing the quick-release cartridge into the quick-release atomizer assembly, or vice versa. The engagement process allows the quick-release cartridge to couple to the quick-release atomizer assembly in a substantially instantaneous step, and in a secured and sealed fashion while the fluid opening is uncovered or unsealed from the spring-loaded trapdoor in the process.

The engaged quick-release mechanism is configured to attach to a microvaporizer on the base end of the quick-release atomizer assembly. In addition, the top end of the quick-release cartridge is configured to attach to a mouthpiece that can provide vapor to a user. The engaged quick-release mechanism is shown to have a cylindrical shape in the figures. In alternative embodiments, the engaged quick-release mechanism can have a non-conformed shape, for example, the quick-release cartridge can have a different external shape than the quick-release atomizer assembly, so long as the inner parts of the quick-release cartridge and quick-release atomizer assembly can correspond and engage to one another.

When it is desired to remove the cartridge from the atomizer assembly, for example, when a user wants to exchange or replace the cartridge, the quick-release mechanism provides a simplified and quick process to disengage the cartridge from the atomizer assembly.

Referring to the embodiment shown in FIGS. 2A and 2B, to disengage the quick-release mechanism, i.e. removing the quick-release cartridge from the quick-release atomizer assembly (to return to the resting position shown in FIGS. 1A and 1B), the process involves:

1. Moving the collar 271 to disengage the first ring 265 from the groove or depression 215.

When the collar 271 is moved towards the base end 253 of the quick-release atomizer assembly 250, the collar 271 releases the first ring 265 from the groove or depression 215 on the root portion extension 214. The first ring 265 is allowed to move slightly radially outwards of the receiver mechanism 277 towards the collar 271. The movement depresses the collar spring 269, and allows the collar to be released from the second ring 267, then catch onto the first ring 265 to be held in place by the first ring 265 and the depressed collar spring 269.

2. Removing the root portion extension 213 from the receiver mechanism 277.

When the collar 271 releases the first ring 265 from the groove or depression 215, the root portion extension 214 is released from the receiver mechanism 277, and is allowed to be removed or pulled out of the receiver chamber 275. The removal of the root portion extension 214 also allows the chamber spring 269 to decompress and move the chamber hatch 263 towards the insertion end 251 of the quick-release atomizer assembly 250, to reseal the opening of the receiver chamber 277.

3. Uncoupling the heating element extension 259 from the spring-loaded trapdoor 217.

The movement of removing the root portion extension 214 from the receiver mechanism 277 also triggers the movement of the heating element extension 259 towards the base end 253 of the quick-release atomizer assembly 250. The removal of the heating element extension 259 out of the through passage 231 allows the release of the spring 221 in the spring-loaded trapdoor 217. The released spring 221 pushes the cover plate 219 back towards the bottom end 203 of the quick-release cartridge 200 to cover over and reseal the fluid opening 211 in the inner casing 207.

The disengagement process of the quick-release mechanism allows a user to remove the cartridge from the atomizer assembly by moving the collar, which simultaneously triggers three movements in the quick-release mechanism. The removal process of the quick-release mechanism not only disengages the cartridge from the atomizer assembly, but also simultaneously reseals the cartridge to avoid fluid leakage during the exchange of cartridges.

Any of the above described alternative embodiments can be similarly engaged and disengaged using the corresponding alternative elements. The quick-release mechanism provides the user with a simplified process for engaging and disengaging the cartridge and atomizer assembly: by the act of pushing the cartridge and atomizer together, the seals are opened and the cartridge and atomizer are locked together, and by the act of moving the collar, the cartridge and atomizer are unlocked from each other and the seals are closed. In addition, the quick-release mechanism provides additional barriers between the coupled parts that helps avoid fluid leakage from the quick-release cartridge when the fluid opening is opened.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

The invention claimed is:

1. A quick-release cartridge for a microvaporizer comprising:
    an outer casing;
    an inner casing radially inward of the outer casing, and having a smaller diameter than a diameter of the outer casing;
    a top surface spanning and fixed to both the outer casing and the inner casing at an upper end section of the cartridge;
    a root portion including a bottom surface spanning and fixed to both the outer casing and the inner casing;
    a fluid storage chamber formed between the outer casing, the inner casing, the top surface and the bottom surface, wherein the fluid storage chamber is sealed by the outer casing, the inner casing, the top surface and the bottom surface;
    at least one fluid opening provided in the inner casing and providing fluid communication from the fluid storage chamber to a passage within the inner chamber and having an opening through the top surface;
    a root portion extension attached to the root portion and extending below the bottom surface, wherein the root portion extension is configured to connect to an atomizer assembly;
    a groove or depression provided on an exterior surface of the root portion extension, wherein the groove or depression is configured to receive a locking component of the atomizer assembly; and
    a spring-loaded trapdoor adjacent and covering surface of the inner casing which includes the at least one fluid opening, wherein the spring-loaded trap door is configured to move in an axial along the surface of the inner casing between a first position at which the spring-loaded trapdoor is configured to seal the at least one fluid opening and a second position which exposes the at least one fluid opening to provide fluid communication between the fluid storage chamber and a through passage within the inner passage and extending through the top surface to an upper opening of the cartridge,
    wherein the spring-loaded trapdoor is configured to be moved from the first position to the second position by connecting the atomizer assembly to the root portion extension.

2. The quick-release cartridge of claim 1 further comprising additional grooves or depressions on the root portion extension.

3. The quick-release cartridge of claim 1, wherein, at an engaged position, the trapdoor is configured to move in an axial direction towards the top surface of the cartridge to the second position.

4. The quick-release cartridge of claim 1, wherein the spring-loaded trapdoor includes a spring and a cover plate, and at an engaged position, the spring is depressed between a protrusion on the radially inner surface of the inner casing and a protrusion on the cover plate, and the cover plate moves axially towards the top surface to the second position.

5. The quick-release cartridge of claim 1 further comprising a through passage on the radially inner portion of the quick-release cartridge, inside the inner casing.

6. The quick-release cartridge of claim 5, wherein the spring-loaded trapdoor extends along and abuts the through passage.

7. A quick-release mechanism having a quick-release cartridge and a quick-release atomizer assembly, comprising:
a quick-release cartridge having a top end and a bottom end, including an inner casing, an outer casing having a diameter that is larger than a diameter of the inner casing, a spring-loaded trapdoor provided along the radially inner surface of the inner casing, a fluid storage chamber defined in between the outer casing and the inner casing, at least one fluid opening provided on the inner casing, and a groove or depression provided on an extended root portion at the bottom end of the cartridge; and
a quick-release atomizer assembly having an insertion end and a base end, including a base portion at the base end, a heating element connected to the base portion having a heating element extension that extends from the base portion towards the insertion end, and a receiver mechanism supported by the base portion and located radially outwards of the heating element;
wherein the groove or depression on the extended root portion is configured to attach to the receiver mechanism when the quick-release cartridge and the quick-release atomizer assembly are coupled together.

8. The quick-release mechanism of claim 7, wherein the receiver mechanism includes a chamber spring provided in a receiver chamber defined by a chamber support, the receiver chamber is sealed by a chamber hatch that is configured to depress the spring when the chamber hatch is pushed into the receiver chamber, a locking component provided in the chamber support in close proximity to the chamber hatch, and a collar provided along a radially outer portion of the receiver mechanism configured to move the locking component towards the groove or depression to lock the groove or depression in the receiver mechanism.

9. The quick-release mechanism of claim 8, wherein, at the engaged position, the extended root portion is inserted into the receiver chamber by pushing the chamber hatch into the receiver chamber, and the groove or depression on the extended root portion is held in place by the locking component when the collar is moved axially towards the cartridge simultaneously when the chamber hatch is pushed into the receiver chamber.

10. The quick-release mechanism of claim 8, wherein the locking component is a ring mechanism or a ball mechanism.

11. The quick-release mechanism of claim 8, wherein the collar is moved by a collar spring provided between the collar and the chamber support, the collar is moved when the chamber hatch is pushed into the receiver chamber, and after the collar is moved, the collar is held in place by a second locking mechanism located in close proximity to the locking mechanism and the chamber hatch.

12. The quick-release mechanism of claim 7, wherein the collar engages a second locking mechanism in the receiver mechanism that holds the collar.

13. The quick-release mechanism of claim 7, wherein, at a resting position when the cartridge is not engaged with the atomizer assembly, the spring-loaded trapdoor of the cartridge seals over the fluid opening on the inner casing.

14. The quick-release mechanism of claim 7, wherein, at the engaged position, the heating element extension pushes the spring-loaded trapdoor in an axial direction towards the top end of the cartridge, and the fluid opening is exposed to provide fluid communication from the fluid chamber.

15. The quick-release mechanism of claim 14, wherein, when the atomizer assembly disengages from the cartridge and return to a resting position, the heating element extension releases the spring-loaded trapdoor, and the spring-loaded trapdoor reseals the fluid opening.

16. The quick-release mechanism of claim 7, wherein the cartridge is a single-use and disposable unit.

17. The quick-release mechanism of claim 7, wherein the coupling of the quick-release cartridge and the quick-release atomizer assembly simultaneously moves the spring-loaded trapdoor and unseals the fluid opening, inserts the extended root portion into the receiver mechanism, and locks the extended root portion in the receiver mechanism.

18. A method to engage a quick-release cartridge with a quick-release atomizer assembly, comprising:
providing a quick-release cartridge for a microvaporizer, the cartridge having a top end and a bottom end, including an inner casing, an outer casing having a diameter that is larger than a diameter of the inner casing, a spring-loaded trapdoor extending along the radially inner surface of the inner casing, a fluid storage chamber defined in between the outer casing and the inner casing, at least one fluid opening provided on the inner casing as an opening to the fluid storage chamber, and a groove or depression on a root portion extension located at the bottom end of the cartridge;
providing a quick-release atomizer assembly to engage with the quick-release cartridge, the quick-release atomizer assembly having an insertion end and a base end, including a base portion at the base end, a heating element connected to the base portion having a heating element extension that extends towards the insertion end, and a receiver mechanism provided on the base portion that is located radially outwards of the heating element;
inserting the heating element extension from the atomizer assembly into a through passage radially inwards of the inner casing;
pushing the spring-loaded trapdoor in an axial direction towards the top end of the cartridge when the heating element extension is inserted;
exposing the at least one fluid opening when the spring-loaded trapdoor is pushed;
inserting the extended root portion into the receiver mechanism; and
locking the extended root portion in place within the receiver mechanism.

19. The method of claim 18, wherein the heating element extension and the extended root portion are inserted simultaneously into the through passage and the receiver mechanism, respectively, and the fluid opening is exposed at the same time as the insertions.

20. The method of claim 18, wherein the atomizer assembly further comprises a collar provided radially outwards of the receiver mechanism.

21. The method of claim 18, wherein locking of the extended root portion involves locking a groove or depression on the extended root portion with a ring or a ball in the receiver mechanism.

22. The method of claim 21 further comprising disengaging the quick-release cartridge from the quick-release atomizer assembly by moving the collar in an axial direction towards the base portion to release the extended root portion from the receiver mechanism.

\* \* \* \* \*